United States Patent
Siol et al.

(10) Patent No.: US 6,602,963 B2
(45) Date of Patent: Aug. 5, 2003

(54) POLYESTERS CONTAINING (METH) ACRYLATE END GROUPS

(75) Inventors: Werner Siol, Darmstadt (DE); Peter Pokinskyj, Rossdorf (DE)

(73) Assignee: Merck Patent GmbH, Berlin (DE)

( * ) Notice: Subject to any disclaimer, the term of this patent is extended or adjusted under 35 U.S.C. 154(b) by 25 days.

(21) Appl. No.: 10/043,221

(22) Filed: Jan. 14, 2002

(65) Prior Publication Data

US 2002/0132961 A1 Sep. 19, 2002

(30) Foreign Application Priority Data

Jan. 13, 2001 (DE) .......................... 101 01 387

(51) Int. Cl.⁷ .................. C08F 20/10; C08G 63/06; A61F 13/00
(52) U.S. Cl. ................ 525/437; 528/361; 525/444; 424/422; 424/424; 424/426; 424/443; 424/484
(58) Field of Search .................. 528/361; 525/437, 525/444; 424/422, 424, 443, 426, 484

(56) References Cited

U.S. PATENT DOCUMENTS

| | | |
|---|---|---|
| 4,412,063 A | 10/1983 | Heitz et al. |
| 4,731,425 A | 3/1988 | Ritter |
| 4,795,823 A | 1/1989 | Schmitt et al. |
| 5,290,852 A | 3/1994 | Vyvoda |
| 5,491,244 A | 2/1996 | Ayorinde et al. |
| 5,693,321 A | 12/1997 | Klaveness et al. |
| 5,929,177 A | 7/1999 | Kataoka et al. |

FOREIGN PATENT DOCUMENTS

| | | |
|---|---|---|
| DE | 35 10 035 A1 | 9/1986 |
| EP | 0 663 386 A1 | 7/1995 |

*Primary Examiner*—Samuel A. Acquah
(74) *Attorney, Agent, or Firm*—Millen, White, Zelano, Branigan, P.C.

(57) ABSTRACT

The invention describes polyesters containing (meth) acrylate end groups, of the general formula (I) $CH_2=CRCOO-PE-OCOCR=CH_2$ where $R=CH_3$ or H, where $PE=[-A-OCO-B-COO-]_m-A-, [-CHR'-COO-]_n-A-[-OCOCHR'-]_n$, or combinations thereof, in which A is an alkylidene radical having 2–20 carbon atoms or an alkoxylidene radical having 2–1000, preferably 2–500, alkoxylidene units, B is a saturated alkylidene radical having 2–10 carbon atoms, R' is H or $CH_3$, m is 1–100, n is 1–100, and, if both m and n are present, the sum m+n is 2–200, where the polyesters containing (meth) acrylate end groups are characterized in that a) the content of short-chain di(meth)acrylates (II) $CH_2=CRCOO-A-OCOCR=CH_2$ is <5% by weight, b) the content of hydroxyl groups is <0.25 mol/mol of (meth)acrylate, and c) the APHA color number is <200.

22 Claims, No Drawings

POLYESTERS CONTAINING (METH) ACRYLATE END GROUPS

The invention relates to polyesters containing (meth) acrylate groups as defined by the formula (I) $CH_2=CRCOO-PE-OCOCR=CH_2$ wherein R and PE are as defined herein.

Methacrylic acid esters of polyhydric alcohols are extensively used in industry as crosslinking monomer building blocks. In order to cover the widest possible variety of industrial requirements, virtually all alkanediols available industrially have in this connection been converted into the corresponding methacrylic acid esters, and likewise a large number of ethylene glycols and propylene glycols are also available as methacrylic acid esters, for example diethylene glycol dimethacrylate or polypropylene glycol dimethacrylate.

By contrast, polyesterdiols containing methacrylate end groups or acrylate end groups (generally: (meth)acrylate end groups) play only a secondary role. Whereas polyesterdiols are of considerable importance as soft segments for building up polyurethanes, the corresponding polyesterdiols containing (meth)acrylate end groups have no significant importance. This is all the more amazing since these polyesters are generally readily available and have a good plasticiser action, good optical properties and good weathering resistance. This misunderstanding is attributable primarily to the classical synthetic routes for (meth)acrylic acid esters. Thus, the synthesis of (meth)acrylic acid esters starting from alcohol and (meth)-acryloyl chloride plays only a secondary role, in particular due to the necessity for binding the liberated HCl and owing to the formation of chlorine-containing by-products.

The (meth)acrylic acid esters are primarily formed by direct esterification of the corresponding alcohols with methacrylic acid or acrylic acid or in particular by transesterification of the alcohols with methyl methacrylate or methyl acrylate with the aid of a basic or organotin catalyst (see, for example, DD 272067 or EP 663 386). In this esterification, the polyester is of course also transesterified, at least partially, the consequence that considerable isomerisation of the polyester takes place. By contrast, the α,ω-hydroxyl groups of the polyesterdiols react selectively and rapidly with isocyanates, which means that they can readily be used for building up polyurethanes. In this way, for example by reaction with isocyanatoethyl methacrylate or by reaction with a diisocyanate followed by reaction with hydroxyethyl methacrylate, polyesterurethane methacrylates are obtainable in a simple manner (see J. M. S.-Rev. Macromol. Chem. Phys., C33 (2)m 147–180 (1993), Current Status of Urethane (Meth)acrylate Oligomers and Polymers).

The reaction of polyesters containing carboxyl end groups with glycidyl methacrylate proceeds with similar selectivity, in this case giving polyesters containing methacrylate end groups, but also hydroxyl groups.

The direct introduction of the methacryloyl group, for example in the course of living polymerisation for the synthesis of polymers containing α,ω-dimethacrylate groups, has also been described. Thus, Heitz et al. (U.S. Pat. No. 4,412,063) produces a polytetrahydrofuran containing methacrylate end groups by cationic polymerisation in the presence of methacrylic anhydride.

Kataoka et al. (U.S. Pat. No. 5,929,177) describe the build-up of a block copolymer $X-O-(-CH_2-CH_2-O-)_m-(Y)_n-Z$ by living polymerisation starting from a polyvalent, functional, for example amino group-containing central group X, where firstly a polyethylene oxide block, then a polymethacrylate or polyester block Y is produced and finally a methacryloyl group is introduced by termination using, for example, methacrylic anhydride. Block copolymers of this type containing polymerisable end groups and a polar central function X are suitable, for example, for building up specific polymerisable surfactants. Polyesters containing $-O-CH_2-O-$ units and (meth) acrylate end groups which have particularly good biodegradability are described by Klaveness et al. (U.S. Pat. No. 5,693,321).

If a specific chain-length distribution and high end-group functionality are not important, the (meth)acrylate end groups can also be introduced directly during synthesis of the polyesters. Thus, Vyvoda (U.S. Pat. No. 5,290,852) describes the concomitant use of 2-hydroxyethyl methacrylate, methacrylic acid or methacrylic anhydride as monofunctional end groups in the synthesis of a polyester based on glutaric acid. These polyester mixtures are employed in the polymerisation of vinyl chloride for the preparation of internally plasticised PVC.

Schmitt et al. (U.S. Pat. No. 4,795,823) describe the synthesis of an α, ω-methacrylate-containing polyester based on triglycolic acid and T-diol (abbreviation for a diol having a complex structure) starting from an oligoester and methacrylic acid. The oligoester containing methacrylate end groups, but also 32% of the T-diol dimethacrylate are found here. This ester/polyester mixture is employed as dental material.

A considerable proportion of short-chain alkanediol esters is also found in the direct esterification of polylactide with methacrylic acid. In addition, these polyesters obtained by direct esterification of a polylactide with methacrylic acid are intensely colored (see U.S. Pat. No. 4,731,425 and Comparative Example 1).

A particularly gentle synthesis of acrylic acid esters is described by Ayorinde et al. (U.S. Pat. No. 5,491,244), which gives access to a sensitive epoxyacrylic anhydride. This synthesis is carried out without any catalyst and with a 4-fold excess of acrylic anhydride.

By contrast, the synthesis of methacrylic acid esters starting from methacrylic anhydride and various α-hydroxycarboxylic acid esters (lactic acid esters) proceeds significantly less well. In spite of catalysis with sulfuric acid, an excess of methacrylic anhydride and heating at 130° C. for 5 hours, a conversion of only about 50% is achieved. In addition, problems arise in separating off the unreacted anhydride (see Rehberg et al., Journal of the American Chemical Society, Vol 67, 210 (1945)).

There continues to be a demand for polyesters containing (meth)acrylate end groups, for example for building up low-shrinkage systems or in the area of two-component adhesives. Of particular interest are polyesters containing polymerisable (meth)acrylate end groups based on poly-α-hydroxycarboxylic acids (for building up copolymers containing degradable lactide branches, see, for example, Sandner et al., Macromol. Symp. 1996, 103 (Polymer and Medicine), 149–62).

In order to ensure good biodegradability, the content of short-chain di(meth)acrylates without an ester group between the (meth)acrylate end groups should be as low as possible.

There is likewise a demand for chlorine-free, transparent, amorphous polyesters containing (meth)acrylate end groups which have the highest possible functionality and are of high optical quality and which, like the polyesterdiols of polyurethanes, are suitable as weathering-stable soft segment for building up poly(meth)acrylate systems.

There is a demand for (meth)acrylates functionalised in this way for the following specific applications in medical technology:

adhesive bonding of endogenous hard tissue, for example anatomical reposition, fixing and retention of bone fragments in comminuted fractures and joint fractures augmentation of osteosynthesis material made from metal or plastic (screws, pins) in bones, particularly in osteoporotic bones, for improving mechanical stability adhesive bonding of endogenous soft tissue into hard tissue, for example in the fixing of tendons and ligaments into drilled holes in bones production of highly porous moldings for implantation in bone production of composite materials by mixing with ceramic or salt-like substances, such as, for example, hydroxylapatite or calcium phosphates dental material, for example also prefabricated moldings (inserts)

dental lacquer base material for implantable active-ingredient carriers absorbable membrane for covering bone defects material for the production of implants for filling relatively large bone defects, for example after tumour resection material for use of absorbable implants produced by rapid prototyping

SUMMARY OF THE INVENTION

It has now been found that the requirements of industry, in particular the requirements regarding degradability, weathering resistance, mechanical and optical properties, are satisfied in an excellent manner by polyesters containing (meth)acrylate end groups, of the general formula (I)

$$CH_2=CRCOO-PE-OCOCR=CH_2 \quad (I)$$

where R=CH$_3$ or H where PE=[—A—OCO—B—COO—]$_m$—A—, [—CHR'—COO—]$_n$—A—[—OCOCHR'—]$_n$, or combinations thereof, in which A is an alkylidene radical (e.g., —(CH$_2$)$_k$—) having 2–20 carbon atoms or an alkoxylidene radical (e.g., —(C$_2$H$_4$O)$_{L-1}$—C$_2$H$_4$— where L is 2–500) having 2–1000, preferably 2–500, alkoxylidene units, wherein each alkoxylidene unit preferably has at least 2 to 3 carbon atoms as a repeating unit, B is a saturated alkylidene radical having 2–10 carbon atoms, R' is H or CH$_3$, m is 1–100, n is 1–100, wherein if PE is a combination of [A—OCO—B—COO—]$_m$—A— and [CHR'—COO—]$_n$—A—[—OCOCHR'—]$_n$ then the sum m+n is 2–200, where the polyesters containing (meth)acrylate end groups are characterised in that a) the content of short-chain di(meth)acrylates (II)

$$CH_2=CRCOO-A-OCOCR=CH_2 \text{ is } <5\% \text{ by weight}, \quad (II)$$

b) the content of hydroxyl groups is <0.25 mol/mol of (meth)acrylate, and c) the APHA color number is <200.

The low content of short-chain di(meth)acrylates (II) prevents the otherwise soft networks from becoming brittle and ensures degradability, for example by hydrolysis of the PE ester groups.

The low content of hydroxyl groups results on the one hand in a high content of crosslinking-active diesters, and secondly the absence of relatively large proportions of hydroxyl groups also effects low absorption of water.

Finally, the low yellow coloring guarantees the synthesis of high-quality optical components and enables good and especially reproducible colorability, for example in the area of repair materials.

The term polyester PE here is taken to mean polyesters and oligoesters having a molecular weight in the range 200–20,000, preferably 300–8,000 and particularly preferably in the range 400–4000 daltons. Regarding the polyesters, those based on α-hydroxycarboxylic acids, such as glycolic acid and lactic acid, are preferred over polyesters based on other hydoxycarboxyclic acids and over polyesters based on alkanediols and saturated dicarboxylic acids. Particular preference is given to lactides. Other hydroxycarboxylic acids, such as, for example, polyhydroxybutyric acid, are not according to the invention.

In general, m and n are numbers from 2 to 100, where, in particular, even-numbered values for n are preferred. There is particular interest in oligolactides in the range n=2–20 and preferably n=2–8. For m, values of 2–20, in particular 2–10, are preferred.

A is the alkylidene radical of an alkanediol having 2–20 carbon atoms. This branched or unbranched alkanediol HO—A—OH contains no double bonds and, apart from ether groups, contains no heteroatoms, in particular no nitrogen atoms.

Examples of possible alkanediols HO—A—OH which may be mentioned are the following: ethanediol, di-, tri- and tetraethylene glycol, oligo- and polyethylene glycols up to a molecular weight of up to 20,000 daltons, propylene glycol, 1,3- and 1,4-butanediol, 1,5-pentanediol, 1,6-hexanediol, 2,2-dimethyl-1,3-propanediol, as well as 2,2,4-trimethyl-1, 6-hexanediol and 2-methyl-1,3-propanediol. Alkanediols containing no tert-CH groups are preferred here.

B is the alkylidene radical of a saturated dicarboxylic acid. B is an alkylidene radical having 2–10 carbon atoms. Representatives of this group HOOC—B—COOH which may be mentioned are, in particular, the following: succinic acid, glutaric acid, adipic acid, azelaic acid, sebacic acid and decanedicarboxylic acid, which are unsubstituted or substituted by methyl groups, and mixtures of these acids.

While ethanediol and diethylene glycol are particularly preferred in the case of polylactides, ethanediol is of less interest in the case of polyesters PE made from dicarboxylic acids HOOC—B—COOH and alkanediols HO—A—OH. Particular mention should be made here of butanediol, hexanediol, diethylene glycol and 2,2-dimethyl-1,3-propanediol. Particular preference is given to polyesters PE containing at least two different alkanediols HO—A—OH, one of the alkanediols generally being branched. An example which may be mentioned is the following:

poly(1,4-butanediol/2,2-dimethyl-1,3-propanediol )-alt-adipic acid.

In these polyesters containing two different diols, the branched radical generally prevents crystallisation and thus allows the synthesis of amorphous, highly transparent products.

In principle, the polyesters made from dicarboxylic acids HOOC—B—COOH and alkanediols HO—A—OH may also have been modified by hydroxy-carboxylic acids, for example lactic acid. However, preference is given to polyesters built up only from dicarboxylic acids and diols.

In principle, the functionality of the polyesters PE can be increased through a certain proportion of trifunctional alkanols, for example trimethylol-propane. In general, however, the proportion of trifunctional compounds of this type is less than 10% by weight, preferably <1% by weight. Particular preference is given to polyesters PE which contain no trifunctional alkanols.

A particular characteristic of the polyesters according to the invention containing (meth)acrylate end groups is to be seen in the good optical properties.

Thus, the yellowness index or APHA color number is <200, generally <100, preferably <50 (cf. DIN 53409). Under certain circumstances, the omission of heteroatoms of any type, the absence of any aromatic structures and readily oxidisable groups contribute to the particular brilliance of the polyesters according to the invention containing methacrylate end groups.

The number of suitable stabilisers is also an essential feature; thus, in particular, hydroquinone or hydroquinone monomethyl ether should be limited to a content of <100 ppm. Particular preference is given to polyesters containing methacrylate end groups which contain <1 ppm of these phenols or better do not contain these phenols at all.

The polyesters according to the invention containing (meth)acrylate end groups are also distinguished by a particularly low content of hydroxyl groups. This primarily squeezes out the high content of (meth)acryloyl end groups. Essential for these polyesters containing (meth)acrylate end groups is a ratio of free hydroxyl groups to (meth)acrylate end groups of <0.25 or better <0.2 or particularly preferably <0.15. Particularly good product properties arise if the ratio between free hydroxyl groups and methacrylate end groups is <0.1 or even more favourably <0.06. In general, the content of free hydroxyl groups is determined through the hydroxyl number. In addition, other methods, such as, for example, NMR, are also suitable. Thus, for example, the hydroxyl number is determined in accordance with DIN ISO 4629.

In general, the hydroxyl number is <68 mg of KOH/g of polyester containing (meth)acrylate end groups. The hydroxyl number is naturally smaller the greater the molecular weight of the polyester containing (meth)acrylate end groups. The following applies as a rule of thumb:

| Molecular weight of the polyester (Mw) | Hydroxyl number (mg of KOH/g of polyester (I)) |
|---|---|
| 500 | <68 preferably <34 |
| 1000 | <34 preferably <17 |
| 2000 | <17 preferably <8 |
| 4000 | <8 preferably <4 |

Also of importance is the lowest possible content of short-chain diesters (II). Thus, the lowest possible content of these diesters (II) prevents firstly the products produced therewith becoming brittle, and secondly a particularly low content of (II) also ensures biodegradation of the products. In addition, polyesters containing no low-boiling components are safer to handle, in particular they exhibit no odour nuisance at all. For this reason, the solvent content should also be kept low. In general, the solvent content is <20% by weight, preferably <5% by weight. The polyester according to the invention containing (meth)acrylate end groups particularly preferably contains no solvent at all.

By contrast, polyesters containing (meth)acrylate end groups which contain small proportions of polymerisable monomers are in accordance with the invention. A monomer which may be mentioned here is, in particular, (meth)acrylic acid. Through a content of, for example, 0.5–10% by weight, firstly the rheology of the polyesters can be modified, and secondly the content of (meth)acrylic acid promotes cohesion during later polymerisation and adhesion to a very wide variety of substrates.

The preferred synthesis of the polyesters according to the invention containing (meth)acrylate end groups is carried out without solvents. Thus, in a preferred process, a polyester HO—PE—OH is reacted with methacrylic anhydride in the presence of 0.1–5% by weight of an acidic catalyst to form the polyester containing methacrylate end groups (I) and methacrylic acid.

HO—PE—OH+2CH$_2$=CCH$_3$CO—O—COCCH$_3$=CH$_2$

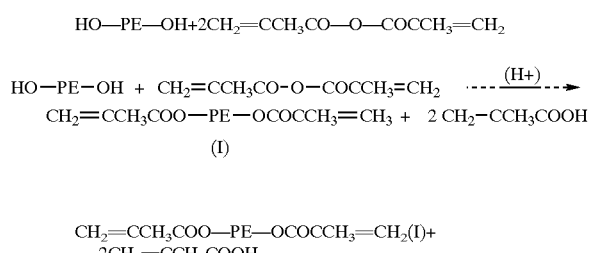

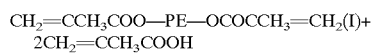

An essential aspect for this synthesis is the presence of the catalyst acid in the above-mentioned concentrations, preferably in the range 0.5–3% by weight and particularly preferably in the range 0.8–2% by weight (in each case based on the methacrylic anhydride employed).

The reaction is carried out at a temperature in the range 0–100° C., preferably in the range 20–80° C. In general, the reaction takes place within 1–48 hours and particularly preferably in the range 4–24 hours. Under these conditions, the ester groups of the polyester HO—PE—OH are not cleaved, meaning that there is likewise no formation of free diols HO—A—OH, which ultimately give the undesired by-product (II) after esterification.

An essential aspect for the highest possible degree of completion of the reaction is a sufficient amount of catalyst acid and sufficient time. An increase in the temperature above 100° C. promotes, in particular, the formation of by-products and should therefore be avoided.

The acidic catalysts used are preferably sulfuric acid, aromatic or aliphatic sulfonic acids, which may be bonded, for example, to a polymer resin, or phosphonic acids.

A particularly suitable starting material for the synthesis of the polyesters according to the invention containing (meth)acrylate end groups is, in particular, a (meth)acrylic anhydride as obtainable by reaction of (meth)-acrylic acid with acetic anhydride. A methacrylic anhydride of this type is described, for example, in DE-A 3510035. A (meth)acrylic anhydride prepared in this way usually contains small proportions of unreacted acetic anhydride and the mixed anhydride of (meth)acrylic acid and acetic acid. In general, a purity of the (meth)acrylic anhydride of 93% or better 96% is adequate. Due to the content of mixed anhydride and the content of acetic anhydride, small proportions of polyesters containing acetic acid ester end groups are obtained in the reaction of HO—PE—OH with the (meth)acrylic anhydride. However, it has been found that a content of polyesters containing acetic acid ester groups of <5% by weight, preferably <2% by weight and very particularly preferably <1% by weight can be tolerated. In contrast to chlorine-containing by-products, which should generally be restricted to a content of <0.1% by weight in the polyesters according to the invention or better should be excluded completely, polyesters containing 0.2–5% by weight of a polyester containing acetyl end groups are in accordance with the invention.

In general, the molar ratio of (meth)acrylic anhydride to hydroxyl groups of the polyesterdiols HO—PE—OH is selected in the region of 1:1. However, the use of a slight sub-stoichiometric amount of (meth)acrylic anhydride (for example 0.95 mol of (meth)acrylic anhydride/1.0 mol of hydroxyl groups) is preferred. This ensures complete reaction of the (meth)acrylic anhydride, making removal of unreacted anhydride superfluous.

In particular in the case of relatively high-molecular-weight polyesterdiols, however, it is also possible to use an excess of (meth)acrylic anhydride, of, for example, 20 mol %. In this case, the excess (meth)acrylic anhydride is destroyed by addition of a low-molecular-weight alcohol, such as methanol, ethanol or isopropanol, after the highest possible degree of reaction of the hydroxyl groups of the polyesterdiol.

In principle, the (meth)acrylic acid formed in the reaction of the polyesterdiol with the (meth)acrylic anhydride can be distilled directly out of the reaction batch. In addition, it is also possible firstly to carry out the reaction to completion, to separate off the catalyst and only then to distil the (meth)acrylic acid out of the batch. This procedure is particularly appropriate in the case of polymer-bound catalyst acids. In any case, the (meth)acrylic acid is separated off under reduced pressure, for example at p<10 mbar. For better stabilisation, air is passed through the reaction batch at the same time. In general, the (meth)acrylic acid is removed from the reaction batch to a content of <10% by weight, preferably <5% by weight and particularly preferably <2% by weight.

In the case of non-polymer-bound catalysts, such as, for example, sulfuric acid or methanesulfonic acid, the catalyst can also be removed by washing with water. The (meth) acrylic acid is removed by distillation.

In order to prevent premature polymerisation, polymerisation inhibitors are added during the reaction; particular mention may be made here of sterically hindered phenols, such as topanol A or ionol. Hydroquinone and hydroquinone monomethyl ether are unsuitable as stabilisers.

Regarding the polyesterdiols, the starting materials used are, in particular, the polyesterdiols used in the area of polyurethane chemistry, with the above-mentioned restrictions regarding A and B (see, for example, Ullmann's Encyclopedia of Industrial Chemistry, Vol. A 21, 228 and 670). However, the lowest possible content of free alkanediol HO—A—OH should be ensured here. Thus, content of HO—A—OH should generally be <3% by weight, preferably <1% by weight and very particularly preferably <0.2% by weight.

In general, polyesters containing (meth)acrylate end groups having the narrowest possible molecular weight distribution are particularly suitable. In general, $M_w/M_n$ should be <2.5, preferably <1.8 and particularly preferably <1.5.

Owing to the extraordinary polymerisation reactivity of the acrylate, reactions according to the invention with acrylic anhydride should only be carried out in at best very small amounts in microreactors.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited above, and of corresponding German patent application No. 101 01 387.6, filed Jan. 13, 2001, are hereby incorporated by reference.

EXAMPLES

The following examples explain embodiments of the polyesters in greater detail.

Very generally, the polyesters according to the invention containing (meth)acrylate end groups can be obtained by degassing the polyesters prepared in the usual manner very carefully under reduced pressure, extracting them with non-solvents or reprecipitating them from solvents/precipitants in order thus to reduce the content of di(meth)acrylate (II) to <5% by weight.

EXAMPLES

Example 1

Synthesis of ethylene glycol oligolactic acid dimethacrylate

PE=[—CHR—COO—]$_n$—A—[—OCOCHR—]$_n$
A=—CH$_2$—CH$_2$—, R=CH$_3$, n=2

In a 1 l three-necked flask, 355 g of methacrylic anhydride (stabilised with 380 mg of ionol) and 466 g of ethylene glycol oligolactic acid ($M_w$=488 g/mol) are mixed at room temperature. After addition of 6.5 g of methanesulfonic acid, the mixture is slowly warmed to 60° C. with stirring. The methacrylic acid formed is then removed by distillation under reduced pressure with an increase in the temperature to about 80° C.

The colorless oil obtained is washed with water, dilute soda solution and then again with water.

For drying, the water present in the product is removed by vacuum distillation.

Yield 591 g of colorless, clear oil

Color number<50 APHA

Ethylene glycol dimethacrylate: 0.17%

Methacrylic acid: 0.87%

Content of methacrylate end groups per ethylene glycol: 1.90

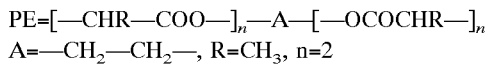

Comparative Example 1

(Not According to the Invention)

The ethylene glycol oligolactic acid employed in Example 1 is esterified with methacrylic acid using methanesulfonic acid as catalyst with removal of the resultant water under reduced pressure.

A brown, cloudy oil results

APHA color number inapplicable,

Ethylene glycol dimethacrylate: 5.6%

Methacrylic acid: 4.3%

Content of methacrylate end groups per ethylene glycol: 1.7

Example 2

Synthesis of poly(1,4-butanediol/2,2-dimethyl-1,3-propanediol-alt-adipic acid) containing methacrylate end groups PE=[—A—OCO—B—COO—]$_m$—A—
A=—CH$_2$—CH$_2$—CH$_2$—CH$_2$—, —CH$_2$—C(CH$_3$)$_2$—CH$_2$—
B=—CH$_2$—CH$_2$—CH$_2$—CH$_2$—

79.7 g of poly(1,4-butanediol/2,2-dimethyl-1,3-propanediol-alt-adipic acid) containing HO end groups (M$_N$: 750 g/mol, Aldrich) is reacted with 36.2 g of methacrylic anhydride with addition of 0.7 g of methanesulfonic acid as catalyst. Washing with water and removal of the resultant methacrylic acid by distillation gives a crystal-clear, colorless oil.

Example 3

Synthesis of diethylene glycol oligolactic acid dimethacrylate
PE=[—CHR—COO—]$_n$—A—[—OCOCHR—]$_n$
A=—CH$_2$—CH$_2$—O—CH$_2$—CH$_2$—, R=CH$_3$, n=2

In a 1 l three-necked flask, 330 g of methacrylic anhydride (stabilised with 320 mg of ionol) and 441 g of diethylene glycol oligolactic acid (M$_w$=479 g/mol) are mixed at room temperature. After addition of 6.4 g of methanesulfonic acid, the mixture is slowly warmed to 50° C. with stirring. The methacrylic acid formed is then removed by distillation under reduced pressure with an increase in the temperature to about 70° C.

The colorless oil obtained is washed with water, dilute soda solution and then again with water.

For drying, the water present in the product is removed by vacuum distillation.

Yield 577 g of a colorless, clear oil
Diethylene glycol dimethacrylate: <0.05
Methacrylic acid: 4.7%
Content of methacrylate end groups per diethylene glycol: 1.45

Example 4

Synthesis of polyethylene glycol 600 oligolactic acid dimethacrylate
PE=[—CHR—COO—]$_n$—A—[—OCOCHR—]$_n$
A=—[CH$_2$—CH$_2$—O]$_n$—CH$_2$—CH$_2$—PEG-600
R=CH$_3$, n=4

The process is analogous to Examples 1 and 3, but the following weights of starting materials are used:
120.5 g of methacrylic anhydride,
487.9 g of polyethylene glycol 600 oligolactic acid (M$_w$= 1188 g/mol)
250 mg of ionol
4.3 g of methacrylic anhydride
4.3 g of methanesulfonic acid The mixture is slowly warmed to 50° C. with stirring. The volatile by-products are then removed by distillation under reduced pressure with an increase in the temperature to 70° C., giving a clear, colorless liquid, which is washed with water, and 63 mg of ionol are added. Drying under reduced pressures gives 346 g of a colorless, clear oil.

Methacrylic acid: 4.7%
Content of methacrylate end groups per PEG 600 unit: 1.96
M$_W$: 1221, M$_N$: 848, M$_W$/M$_N$: 1.44

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A polyester containing (meth)acrylate end groups, of the formula $$CH_2=CRCOO—PE—OCOCR=CH_2 \quad (I)$$

wherein
R is CH$_3$ or H,
PE is [—A—OCO—B—COO—]$_m$—A—, [—CHR'—COO—]$_n$—A—[—OCOCHR'—]$_n$, or combinations thereof,
A is an alkylidene radical having 2–20 carbon atoms or an alkoxylidene radical having 2–1000 alkoxylidene units, each alkoxylidene unit contains 2 to 3 carbon atoms as a repeating unit
B is a saturated alkylidene radical having 2–10 carbon atoms,
R' is H or CH$_3$,
m is 1–100,
n is 1–100, and
when both m and n are both present the sum m+n is 2–200, and wherein
 a) the content of short-chain di(meth)acrylates (II) CH$_2$=CCH$_3$COO—A—OCOCCH$_3$=CH$_2$ is <5% by weight,
 b) the content of hydroxyl groups is <0.25 mol/mol of (meth)acrylate, and
 c) the APHA color number is <200.

2. A polyester according to claim 1, wherein PE is [—A—OCO—B—COO]$_m$—A—.

3. A polyester according to claim 1, wherein PE is [—CHR—COO]$_n$—A—[—OCOCHR—]$_n$.

4. A polyester according to claim 1, wherein said polyester contains 0.5–10% by weight of (meth)acrylic acid.

5. A polyester according to claim 1, wherein said polyester has a molecular weight of between 400 and 4000 daltons.

6. A polyester according to claim 1, wherein said polyester is a lactide.

7. A polyester according to claim 1, wherein said polyester contains no trifunctional alcohols.

8. A polyester according to claim 1, wherein the content of hydroxyl groups is less than 0.20 mol/mol of (meth) acrylate.

9. A polyester according to claim 1, wherein the APHA color number is less than 50.

10. A polyester according to claim 1, wherein the molecular weight distribution M$_w$/M$_N$ is <2.5.

11. A polyester according to claim 1, wherein A is an alkylidene radical having 2–20 carbon atoms or an alkoxylidene radical having 2–500 alkoxylidene units.

12. A polyester according to claim 1, wherein each alkoxylidene unit is —CH$_2$CH$_2$O—.

13. A polyester according to claim 1, wherein each alkoxylidene unit is —CH$_2$CH$_2$CH$_2$O—.

14. A process for the preparation of a polyester according to claim 1, said process comprising:
  reacting diol HO—PE—OH with (meth)acrylic anhydride to form a polyester of formula (I) and (meth)acrylic acid.

15. A process according to claim 14, wherein the reaction is carried out in the presence of an acidic catalyst at a concentration of 0.1–5% by weight.

16. In a process for the for the production of medical products for endoprosthetics, osteosynthesis and wound healing containing a polyester, the improvement wherein said polyester is in accordance with claim 1.

17. In a process for adhesive bonding of endogenous hard and/or soft tissue using a polyester, the improvement wherein said polyester is in accordance with claim 1.

18. In a process for augmentation of osteosynthesis material made from metal or plastic in bone using a polyester, the improvement wherein said polyester is in accordance with claim 1.

19. In a process for production of highly porous moldings for implantation in bone using a polyester, the improvement wherein said polyester is in accordance with claim 1.

20. In a process for production of composite materials using a polyester, the improvement wherein said polyester is in accordance with claim 1.

21. In a process for producing dental lacquer or inserts using a polyester, the improvement wherein said polyester is in accordance with claim 1.

22. In a process of covering bone defects using an adsorbable membrane, the improvement wherein said membrane is made of a polyester according to claim 1.

* * * * *